United States Patent
Ha et al.

(10) Patent No.: US 10,265,196 B2
(45) Date of Patent: Apr. 23, 2019

(54) MOTION ASSISTANCE APPARATUS AND METHOD OF CONTROLLING THE SAME

(71) Applicant: Samsung Electronics Co., Ltd., Suwon-Si, Gyeonggi-Do (KR)

(72) Inventors: Taesin Ha, Seongnam-si (KR); ChangHyun Roh, Seoul (KR); Youngbo Shim, Seoul (KR); Joon-Kee Cho, Yongin-si (KR); Byung-Kwon Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 872 days.

(21) Appl. No.: 14/603,895

(22) Filed: Jan. 23, 2015

(65) Prior Publication Data
US 2016/0022440 A1    Jan. 28, 2016

(30) Foreign Application Priority Data

Jul. 24, 2014 (KR) ........................ 10-2014-0093831

(51) Int. Cl.
*A61F 2/68* (2006.01)
*A61H 3/00* (2006.01)
(Continued)

(52) U.S. Cl.
CPC ................ *A61F 2/68* (2013.01); *A61H 3/00* (2013.01); *A61H 31/00* (2013.01); *B25J 9/0006* (2013.01);
(Continued)

(58) Field of Classification Search
CPC .. A61H 1/00; A61H 1/001; A61H 2001/0207; A61H 2001/0211; A61H 3/00;
(Continued)

(56) References Cited

U.S. PATENT DOCUMENTS 3,226,674 A    12/1965  Eriksson
3,440,602 A    4/1969   Frig
(Continued)

FOREIGN PATENT DOCUMENTS

CN    1838933       9/2006
CN    103200909     7/2013
(Continued)

OTHER PUBLICATIONS

Extended European Search Report for Application No. EP 15 15 7726 dated Dec. 23, 2015.
(Continued)

*Primary Examiner* — Rachel T Sippel
*Assistant Examiner* — Tu Vo
(74) *Attorney, Agent, or Firm* — Harness, Dickey & Pierce, P.L.C.

(57) ABSTRACT

A motion assistance apparatus may include a first fixing member to be fixed to a portion of a user, a second fixing member to be fixed to another portion of the user, a driving source provided in the first fixing member, a power transmitting member connected between the driving source and the second fixing member, a sensing portion to sense a fixing state of the first fixing member or the second fixing member, and a controller to control the driving source based on information received from the sensing portion.

8 Claims, 18 Drawing Sheets

(51) Int. Cl.
*A61H 31/00* (2006.01)
*B25J 9/00* (2006.01)

(52) U.S. Cl.
CPC .............. *A61H 2201/0176* (2013.01); *A61H 2201/165* (2013.01); *A61H 2201/1628* (2013.01); *A61H 2201/1652* (2013.01); *A61H 2201/5025* (2013.01); *A61H 2201/5066* (2013.01); *A61H 2205/088* (2013.01); *A61H 2205/10* (2013.01)

(58) Field of Classification Search
CPC .......... A61H 2003/007; A61H 2201/16; A61H 2201/165; A61H 2201/1652; A61H 2201/5058; A61H 2205/10; A61H 2201/5066; A61H 2201/5025; A61H 2201/0176; A61H 2201/1628; A61F 2/68; B25J 9/0006
See application file for complete search history.

(56) References Cited

U.S. PATENT DOCUMENTS

| | | | |
|---|---|---|---|
| 4,035,595 A | 7/1977 | Tolfsen | |
| 6,317,050 B1* | 11/2001 | Burks | G08B 21/088 340/573.6 |
| 8,221,339 B2 | 7/2012 | Hirata et al. | |
| 2006/0258967 A1* | 11/2006 | Fujil | A61F 5/0102 602/23 |
| 2008/0188907 A1* | 8/2008 | Aguirre-Ollinger | A61H 1/0237 607/48 |
| 2009/0221928 A1* | 9/2009 | Einav | A61B 5/0484 600/544 |
| 2010/0113980 A1* | 5/2010 | Herr | A61F 2/60 600/587 |
| 2011/0071664 A1 | 3/2011 | Linn et al. | |
| 2011/0090079 A1 | 4/2011 | Morino et al. | |
| 2011/0168485 A1* | 7/2011 | Hirata | A44B 11/28 182/3 |
| 2012/0071797 A1* | 3/2012 | Aoki | A61H 1/024 601/34 |
| 2013/0197408 A1* | 8/2013 | Goldfarb | A61F 5/0102 601/35 |
| 2013/0265147 A1 | 10/2013 | Park et al. | |
| 2014/0163435 A1* | 6/2014 | Yamamoto | A61H 3/00 601/35 |

FOREIGN PATENT DOCUMENTS

| | | |
|---|---|---|
| CN | 103356169 | 10/2013 |
| CN | 203417440 | 2/2014 |
| JP | 2006075254 A | 3/2006 |
| JP | 2009284919 A | 12/2009 |
| JP | 2013070784 A | 4/2013 |
| JP | 2014023773 A | 2/2014 |
| KR | 19980052273 | 9/1998 |
| KR | 19990004085 | 1/1999 |
| KR | 20140002303 A | 1/2014 |
| WO | WO-2012/044621 A1 | 4/2012 |
| WO | WO-2014/061269 A1 | 4/2014 |

OTHER PUBLICATIONS

First Office Action issued by The State Intellectual Property Office of P.R. China dated Jun. 21, 2018 for corresponding CN Patent Application No. 201510163500.1.

* cited by examiner

MOTION ASSISTANCE APPARATUS AND METHOD OF CONTROLLING THE SAME

CROSS-REFERENCE TO RELATED APPLICATION

This application claims the priority benefit of Korean Patent Application No. 10-2014-0093831, filed on Jul. 24, 2014, in the Korean Intellectual Property Office, the entire disclosure of which is incorporated herein by reference.

BACKGROUND

1. Field

Example embodiments relate to a motion assistance apparatus and a method of controlling the same.

2. Description of the Related Art

With the onset of rapidly aging societies, an increased number of people may experience inconvenience and/or agony from joint problems, and, therefore, interest in motion assistance apparatuses that may enable the elderly or patients with joint problems to walk with less effort is growing. In addition, motion assistance apparatuses that may increase muscular strength of human bodies may be in development for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

The motion assistance apparatuses may include active joint structures including hydraulic systems and/or driving motors to drive each joint portion to improve muscular strength of legs of the users. For example, a motor to transmit driving power may be provided at each of the hip joint portions.

SUMMARY

Some example embodiments relate to a motion assistance apparatus.

In some example embodiments, the motion assistance apparatus may include a first fixing member to be fixed to a portion of a user, a second fixing member to be fixed to another portion of the user, a driving source provided in the first fixing member, a power transmitting member connected between the driving source and the second fixing member, a sensing portion configured to sense a fixing state of the first fixing member or the second fixing member, and a controller configured to control the driving source based on information received from the sensing portion.

At least one of the first fixing member and the second fixing member may include a first fixing portion and a second fixing portion to be fastened to or separated from each other.

The sensing portion may include a first conductor and a second conductor disposed in the first fixing portion and the second fixing portion, respectively, to be connected or shorted depending on whether the first fixing portion is fastened to the second fixing portion, and the controller may control the driving source based on information about a current flowing between the first conductor and the second conductor.

An elastic member may be disposed on one side of one of the first conductor and the second conductor to provide elastic force in a direction in which another of the first conductor and the second conductor is disposed.

The first fixing portion and the second fixing portion may have faces facing each other and provided detachably, the sensing portion may include a first conductor and a second conductor disposed in the first fixing portion and the second fixing portion, respectively, and the controller may control the driving source based on information about a capacitance between the first conductor and the second conductor.

The first fixing portion and the second fixing portion may be detachably provided in a form of a Velcro.

The sensing portion may include a switch disposed in one of the first fixing portion and the second fixing portion to be selectively powered on or off based on whether the first fixing portion is fastened to the second fixing portion.

The sensing portion may measure a fastening strength of at least one of the first fixing member and the second fixing member.

The sensing portion may include a pressure sensor configured to measure a pressure applied between the user and at least one of the first fixing member and the second fixing member.

The sensing portion may include a tensile force sensor configured to measure a tensile force applied to at least one of the first fixing member and the second fixing member.

The sensing portion may include a tensile force sensor disposed on the power transmitting member.

The sensing portion may include a pressure sensor disposed between the power transmitting member and the second fixing member.

Other example embodiments relate to a method of controlling a motion assistance apparatus.

In some example embodiments, the motion assistance apparatus may include a main fixing member to be fixed to a portion of a user, an action side fixing member to be fixed to another portion of the user, a driving source provided on the main fixing member, a power transmitting member connected between the driving source and the action side fixing member, and a controller configured to control the driving source. Further, the method may include performing, by the controller, a motion assistance operation for the user based on a fixing state of at least one of the main fixing member and the action side fixing member.

The performing may be conducted when both the main fixing member and the action side fixing member are fixed.

The performing may include reducing power to be transmitted to the action side fixing member when the main fixing member is unfixed.

A plurality of action side fixing members may be provided, and the performing may include sensing respective fixing states of the plurality of action side fixing members, and reducing power to be transmitted to a portion of the plurality of action side fixing members when the portion of the plurality of action side fixing members is unfixed.

The performing may include controlling power to be transmitted to the action side fixing member based on a direction of a load applied to the action side fixing member, and the controlling may include continuously performing the motion assistance operation for the user when the load is applied in a direction in which the action side fixing member is pushed, and reducing power to be transmitted to the action side fixing member when the load is applied in a direction in which the action side fixing member is pulled.

The reducing may include stopping the driving source, or reducing an output of the driving source to a predetermined output value.

Other example embodiments relate to a method of controlling a motion assistance apparatus.

In some example embodiments, the motion assistance apparatus may include a driving source, a main fixing member to be fixed to a portion of a user, an action side fixing member to be fixed to a leg of the user, a power transmitting member configured to transmit power between the driving source and the action side fixing member, and a controller configured to control the driving source. Further, the method may include performing, by the controller, a motion assistance operation for the user based on a fixing state of the action side fixing member.

The performing may include reducing power to be transmitted to the action side fixing member when the action side fixing member is unfixed and both legs of the user are in contact with the ground.

The performing may include sensing whether the user is walking in an upward inclined direction or in a downward inclined direction, and transmitting power until both legs of the user are in contact with the ground when the user is walking in a downward inclined direction and the action side fixing member is unfixed.

The performing may include sensing whether the user is walking in an upward inclined direction or in a downward inclined direction, and reducing power to be transmitted to the action side fixing member when the user is walking in an upward inclined direction and the action side fixing member is unfixed.

The performing may include sensing whether a function of the action side fixing member corresponds to a moving function or a supporting function when the action side fixing member is unfixed, and reducing power to be transmitted to the unfixed action side fixing member when the function of the unfixed action side fixing member corresponds to the moving function.

The performing may further include transmitting power until the function of the unfixed action side fixing member is changed to the moving function when the function of the unfixed action side fixing member corresponds to the supporting function.

Some example embodiments relate to a motion assistance apparatus configured to assist a user with walking.

In some example embodiments, the motion assistance apparatus may include a belt having a first end and a second end, the belt configured to attach to a waist of the user by connecting, the first end and the second end; a thigh cuff configured to attach to a thigh of the user; a power transmitting member configured to transmit a torque to the thigh cuff; and a controller including processor and a memory, the memory containing computer readable code that, when executed by the processor, configures the controller to, determine if one or more of the belt and the thigh cuff are secured to the waist and the thigh of the user, respectively, and instruct a driving source to perform a motion assistance operation based on whether the one or more of the belt and the thigh cuff are secured, the motion assistance operation being an operation in which a force generated by the driving source is transmitted to the joint assembly.

In some example embodiments, the motion assistance apparatus includes one or more sensors configured to sense whether one or more of the belt and the thigh cuff are secured, wherein the controller is configured to determine if one or more of the belt and the thigh cuff become unsecured during the motion assistance operation based on signals received from the one or more sensors.

In some example embodiments, the controller is configured to reduce the power based on a walking state, if the controller determines that one or more of the belt and the thigh cuff have become unsecured during the motion assistance operation.

In some example embodiments, the walking state includes an incline walking state and a decline walking state, and the controller is configured to reduce the power when one or more of the belt and the thigh cuff have become unsecured during the motion assistance operation irrespective of whether feet of the user are in contact with a ground, if the walking state is the incline walking state.

In some example embodiments, the controller is configured to stop transmitting the power when one or more of the belt and the thigh cuff have become unsecured during the motion assistance operation and the controller has determined that the user has come to rest.

In some example embodiments, the controller is configured to continue to perform the motion assistance operation on a leg of the user when one or more of the belt and the thigh cuff have become unsecured, if the motion assistance device is exerting positive work on the leg of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
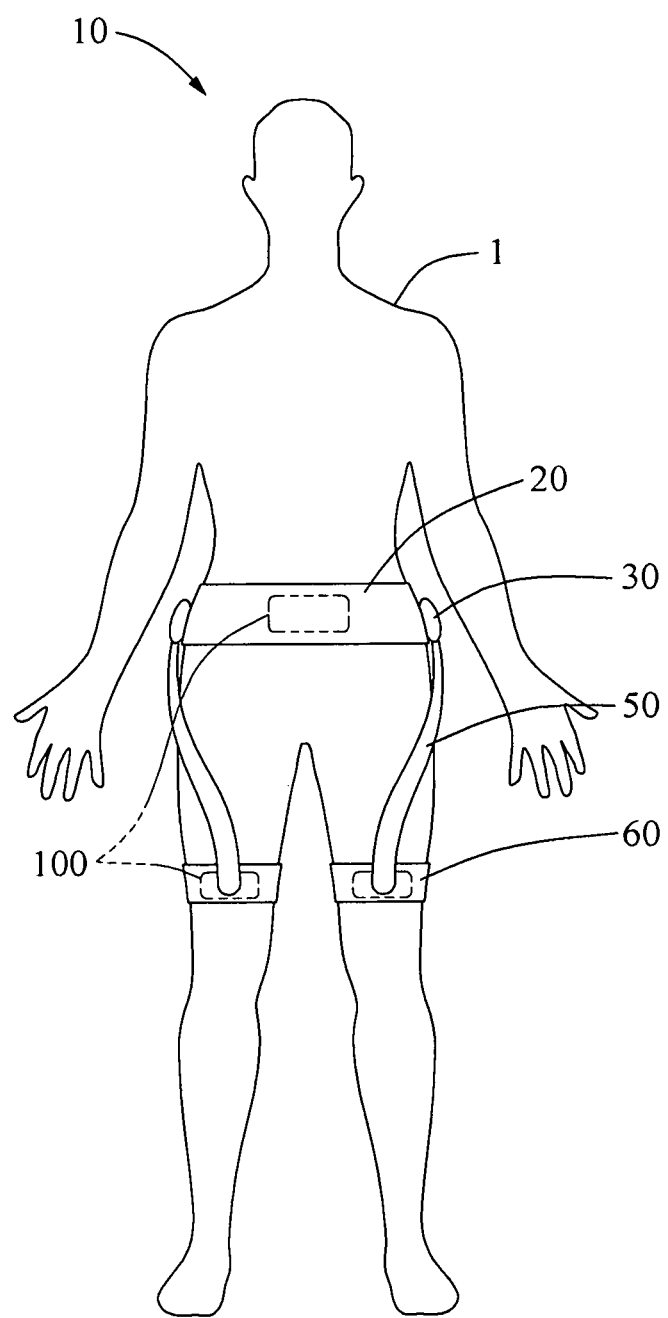
FIG. 1 is a front view illustrating a motion assistance apparatus being worn on a user according to some example embodiments.

Reference will now be made in detail to example embodiments, some examples of which are illustrated in the accompanying drawings, wherein like reference numerals refer to like elements throughout. Example embodiments are described below with reference to the figures.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc, may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between" versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, various features may be exaggerated for clarity.

Figure 2:
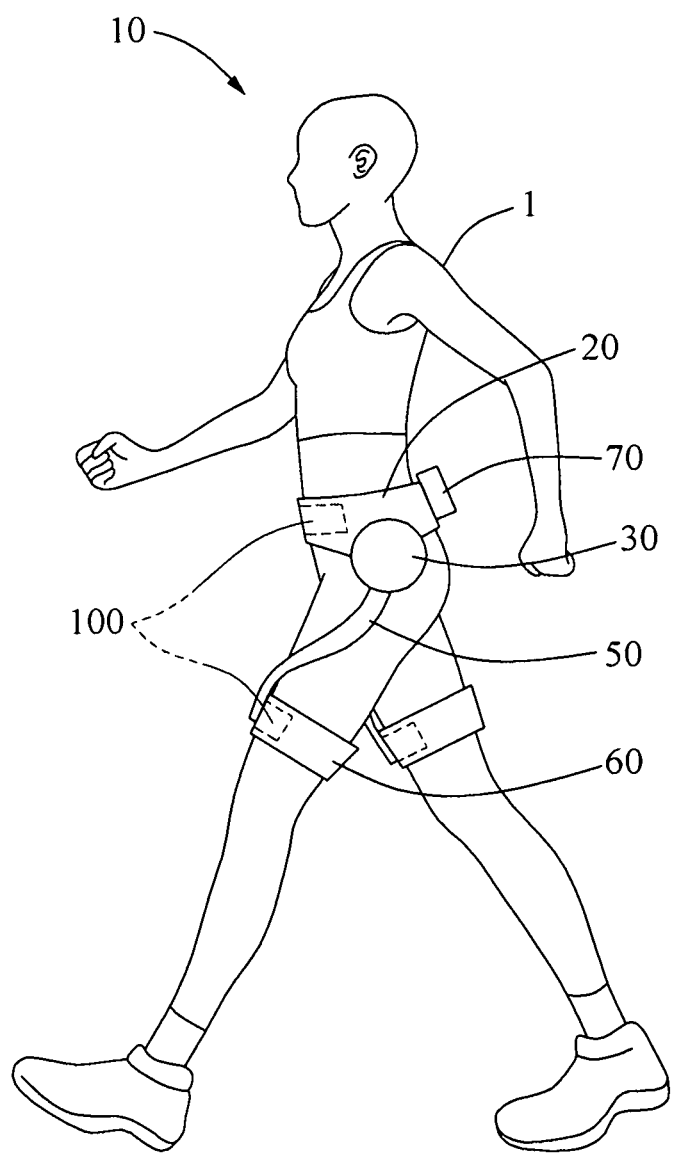
FIG. 2 is a side view illustrating a motion assistance apparatus being worn on a user according to example embodiments.

FIG. 1 is a front view illustrating a motion assistance apparatus 10 being worn on a user 1 according to some example embodiments, and FIG. 2 is a side view illustrating the motion assistance apparatus 10 being worn on the user 1 according to some example embodiments.

Referring to FIGS. 1 and 2, the motion assistance apparatus 10 may be worn on the user 1 to assist a motion of the user 1. The user 1 may correspond to a human, an animal, or a robot. However, the user 1 is not limited thereto. In addition, although FIGS. 1 and 2 illustrate a case in which the motion assistance apparatus 10 assists a motion of a thigh of the user 1, the motion assistance apparatus 10 may also assist the user with motion an upper body part, for example, a hand, an upper arm, and a lower arm of the user 1, or motion of another lower body part, for example, a foot, and a calf of the user 1. The motion assistance apparatus 10 may assist a motion of a part of the user 1. For example, in other example embodiments, the driving source 30 may be provided at the knee joint of the user 1 and the second fixing member 60 may be configured to attach to the shin of the user 1 to transmit a driving force to the shin of the user 1. Hereinafter, a case in which the motion assistance apparatus 10 assists a motion of a thigh of a human will be described, however, example embodiments are not limited thereto.

The motion assistance apparatus 10 includes a first fixing member 20, a driving source 30, a power transmitting member 50, a second fixing member 60, a controller 70, and a sensing portion 100.

The first fixing member 20 may be fixed to a portion of the user 1. The first fixing member 20 may be in contact with at least a portion of an outer surface of the user 1. The first fixing member 20 may be configured to cover the portion of the outer surface of the user 1. The first fixing member 20 may be provided to be curved in a shape corresponding to a contact portion of the user 1. The first fixing member 20 may include a curved surface to be in contact with the user 1. For example, the first fixing member 20 may be fixed to one side of a waist of the user 1. The first fixing member 20 may be referred to as a "waist fixing member". The first fixing member 20 may also be referred to as a "main fixing member".

The driving source 30 may be provided to the first fixing member 20. The driving source 30 may provide power to be transmitted to the power transmitting member 50. For example, a plurality of driving sources may be provided. The driving sources 30 may be provided on both sides of the first fixing member 20, respectively. However, a number or positions of the driving sources 30 is not limited thereto.

The power transmitting member 50 may be connected between the driving source 30 and the second fixing member 60. The power transmitting member 50 may transmit power received from the driving source 30 to the second fixing member 60. The power transmitting member 50 may be, for example, a frame, a wire, a cable, a string, a rubber band, a spring, a belt, and a chain. However, the power transmitting member 50 is not limited thereto.

The second fixing member 60 may be fixed to another portion of the user 1. For example, the second fixing member 60 may be fixed to one side of a leg of the user 1. The second fixing member 60 may be referred to as a "leg fixing member". The second fixing member 60 may be disposed to cover a circumference of at least a portion of the thigh of the user 1 to apply power received from the power transmitting member 50 to the thigh of the user 1.

A plurality of second fixing members 60 may be provided. The plurality of second fixing members 60 may be fixed to both legs of the user 1, respectively. The plurality of second fixing members 60 may respectively rotate with respect to the first fixing member 20. The first fixing member 20 may be referred to as the "main fixing member", and the second fixing member 60 may also be referred to as an "action side fixing member". In the action side fixing member, a fixing member to be fixed to one leg of the user 1 may be referred to as a "first action side fixing member", and a fixing member to be fixed to the other leg of the user 1 may be referred to as a "second action side fixing member".

The controller 70 may control the driving source 30 based on information received from the sensing portion 100.

The sensing portion 100 may sense a fixing state of the first fixing member 20 or the second fixing member 60. For example, the sensing portion 100 may be connected to at least one of the first fixing member 20 and the second fixing member 60. Hereinafter, the sensing portion 100 will be described in detail.

Figure 3:
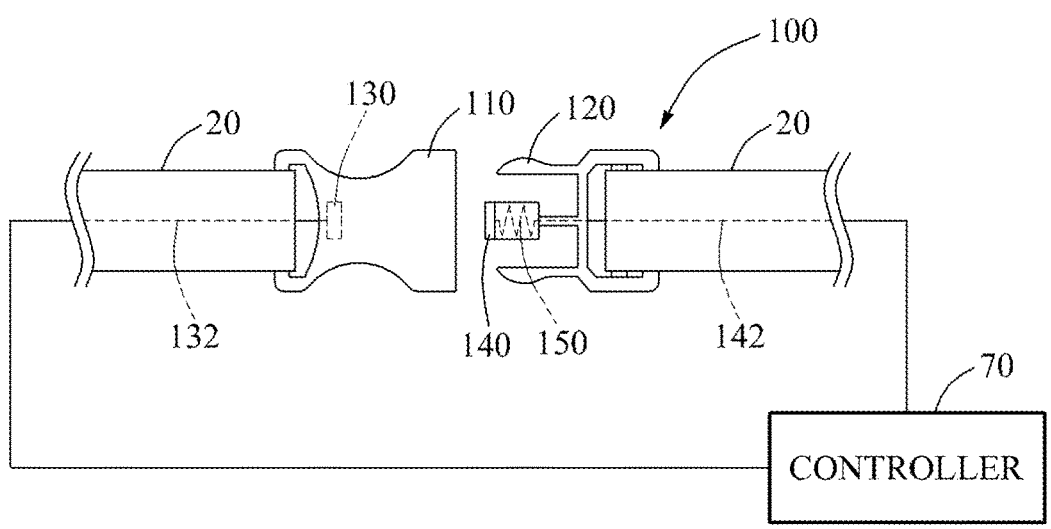
FIG. 3 is a view illustrating a sensing portion according to some example embodiments.

FIG. 3 is a view illustrating the sensing portion 100 according to some example embodiments.

Referring to FIG. 3, the sensing portion 100 may be provided in at least one of the first fixing member 20 and the second fixing member 60. Hereinafter, a case in which the sensing portion 100 is provided in the first fixing member 20 will be described. However, example embodiments are not limited thereto.

The first fixing member 20 includes a first fixing portion 110 and a second fixing portion 120 to be fastened to or separated from each other. For example, the first fixing portion 110 and the second fixing portion 120 may be detachably provided in a structure of a buckle. The second fixing portion 120 may include an insertion portion, and the first fixing portion 110 may include a hanging portion to be releasably inserted into the insertion portion and locked in place by two resilient opposed lateral arms extending away from a center of the insertion portion. The arms may compress upon insertion, thereby providing a spring loading potential energy for their outward expansion. The arms may move into locking slots on the body of the first insertion portion 110 upon full insertion of the insertion portion and spring out into the locked position within the slot.

The sensing portion 100 may include a first conductor 130 and a second conductor 140. The first conductor 130 and the second conductor 140 may be disposed in the first fixing portion 110 and the second fixing portion 120, respectively. The first conductor 130 and the second conductor 140 may be connected to or shorted from each other based on whether the first fixing portion 110 is fastened to the second fixing portion 120.

One side of the first conductor 130 may be connected to the controller 70 with a first wire 132, and another side of the first conductor 130 may be selectively connected to or shorted from the second conductor 140. One side of the second conductor 140 may be connected to the controller 70 with a second wire 142, and another side of the second conductor 140 may be selectively connected to or shorted from the first conductor 130. The first wire 132 and the second wire 142 may be embedded in an internal portion of the first fixing member 20 and, therefore, damage to the first wire 132 and the second wire 142 by an external impact may be prevented.

The sensing portion 100 may further include an elastic member 150. The elastic member 150 may be disposed on one of the first conductor 130 and the second conductor 140. The elastic member 150 may provide elastic force in a direction in which one of the first conductor 130 and the second conductor 140 is disposed with respect to another of the first conductor 130 and the second conductor 140.

The controller 70 may control the driving source 30 based on information about a current flowing between the first conductor 130 and the second conductor 140. For example, when a current flows between the first conductor 130 and the second conductor 140, the controller 70 may determine that the first fixing member 20 is fixed. Thus, the controller 70 may power on the driving source 30. Conversely, when a current does not flow between the first conductor 130 and the second conductor 140, the controller 70 may determine that the first fixing member 20 is unfixed. Thus, the controller 70 may power off the driving source 30.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 4:
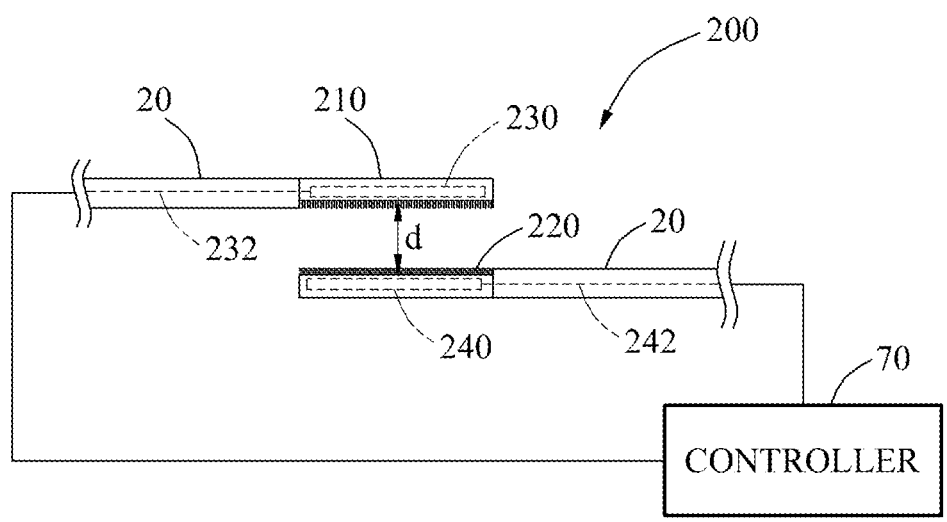
FIG. 4 is a view illustrating a sensing portion according to some example embodiments.

FIG. 4 is a view illustrating a sensing portion 200 according to some example embodiments.

Referring to FIG. 4, the sensing portion 200 may be provided in at least one of the first fixing member 20 and the second fixing member 60. Hereinafter, a case in which the sensing portion 200 is provided in the first fixing member 20 will be described. The first fixing member 20 includes a first fixing portion 210 and a second fixing portion 220 to be fastened to or separated from each other. The first fixing portion 210 and the second fixing portion 220 may have faces facing each other and provided detachably. For example, the first fixing portion 210 and the second fixing portion 220 may be detachably provided in a form of a hook and loop fastener.

The sensing portion 200 may include a first conductor 230 and a second conductor 240. The first conductor 230 and the second conductor 240 may be disposed in the first fixing portion 210 and the second fixing portion 220, respectively. The first conductor 230 and the second conductor 240 may be disposed in an internal portion of the first fixing portion 210 and an internal portion of the second fixing portion 220, respectively, therefore, damage to the first conductor 230 and the second conductor 240 by an external impact may be prevented.

One side of the first conductor 230 may be connected to the controller 70 with a first wire 232. One side of the second conductor 240 may be connected to the controller 70 with a second wire 242. The first wire 232 and the second wire 242 may be embedded in an internal portion of the first fixing member 20.

A capacitance C between the first conductor 230 and the second conductor 240 may be expressed by Equation 1.

$$C = \epsilon \frac{A}{d} \qquad \text{[Equation 1]}$$

In Equation 1, $\epsilon$ denotes a permittivity of a substance between the first conductor 230 and the second conductor 240. A denotes an overlapping area of the first conductor 230 and the second conductor 240 in a vertical direction and d denotes a vertical distance between the first conductor 230 and the second conductor 240.

The distance d may change based on a vertical distance between the first fixing portion 210 and the second fixing portion 220. According to Equation 1, the capacitance C may increase as the distance between the first fixing portion 210 and the second fixing portion 220 decreases. For example, the distance d may be minimized when the first fixing portion 210 and the second fixing portion 220 are attached to each other. Therefore, the capacitance C may be maximum when the first and second fixing portions 210, 220 are attached.

The area A may change based on a difference between a horizontal position of the first fixing portion 210 and a horizontal position of the second fixing portion 220. According to Equation 1, the capacitance C may increase as the overlapping area of the first fixing portion 210 and the second fixing portion 220 increases. For example, the capacitance C may be maximized when the first fixing portion 210 and the second fixing portion 220 completely overlap each other in a vertical direction.

The capacitance C may function as an indicator of a fixing force of the first fixing portion 210 and the second fixing portion 220. Thus, the controller 70 may control the driving source 30 based on information about the capacitance C between the first conductor 230 and the second conductor 240. When the measured capacitance C is greater than a desired (or, alternatively, a predetermined) reference capacitance C0, the controller 70 may determine that the first fixing member 20 is fixed. Thus, the controller 70 may power on the driving source 30. Conversely, when the measured capacitance C is less than the reference capacitance C0, the controller 70 may determine that the first fixing member 20 is unfixed. Thus, the controller 70 may power off the driving source 30.

Figure 5:
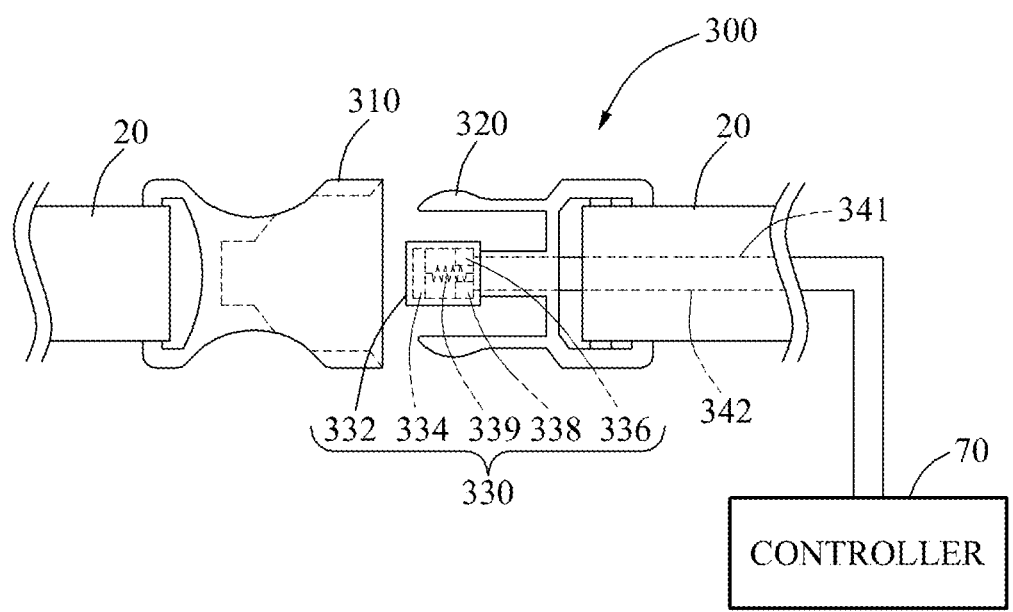
FIG. 5 is a view illustrating a sensing portion according to some example embodiments.

FIG. 5 is a view illustrating a sensing portion 300 according to some example embodiments.

Referring to FIG. 5, the sensing portion 300 may be provided in at least one of the first fixing member 20 and the second fixing member 60. Hereinafter, a case in which the sensing portion 300 is provided in the first fixing member 20 will be described. The first fixing member 20 includes a first fixing portion 310 and a second fixing portion 320 to be fastened to or separated from each other. For example, the first fixing portion 310 and the second fixing portion 320 may be detachably provided in a structure of a buckle. The second fixing portion 320 may include an insertion portion, and the first fixing portion 310 may include a hanging portion to be inserted into the insertion portion.

The sensing portion 300 may further include a switch 330 to be selectively powered on or off based on whether the first fixing portion 310 is fastened to the second fixing portion 320. The switch 330 may be disposed in one of the first fixing portion 310 and the second fixing portion 320. For example, the switch 330 may be disposed in the second fixing portion 320, and be pressurized by the first fixing portion 310. The switch 330 may include a button portion 332, a first conductor 334, a second conductor 336, a third conductor 338, and an elastic member 339.

The button portion 332 may be provided to move slidingly with respect to the second fixing portion 320. The first conductor 334 may be disposed on one side of the button portion 332. The first conductor 334 may selectively connect the second conductor 336 to the third conductor 338 or short the second conductor 336 from the third connector 338 based on whether the first fixing portion 310 is fastened to the second fixing portion 320.

The second conductor 336 and the third conductor 338 may be connected to the controller 70 with a first wire 341 and a second wire 342, respectively. The first wire 341 and the second wire 342 may be disposed in an internal portion of the first fixing member 20.

The elastic member 339 may provide elastic force in a direction in which the first conductor 334 is disposed apart from the second conductor 336 and the third conductor 338.

The controller 70 may control the driving source 30 based on information about a current flowing between the second conductor 336 and the third conductor 338. For example, when a current flows between the second conductor 336 and the third conductor 338, the controller 70 may determine that the first fixing member 20 is fixed. Thus, the controller 70 may power on the driving source 30. Conversely, when a current does not flow between the second conductor 336 and the third conductor 338, the controller 70 may determine that the first fixing member 20 is unfixed. Thus, the controller 70 may power off the driving source 30.

Figure 6:
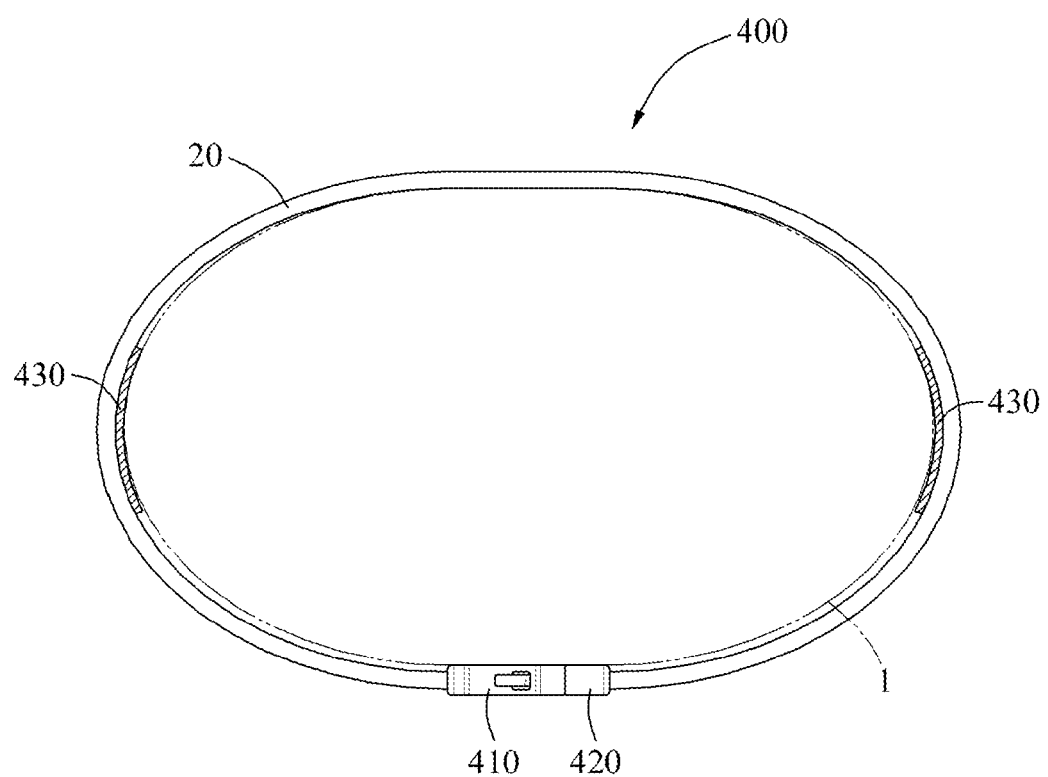
FIG. 6 is a view illustrating a sensing portion according to some example embodiments.

FIG. 6 is a view illustrating a sensing portion 400 according to some example embodiments.

Referring to FIG. 6, the sensing portion 400 may be provided in at least one of the first fixing member 20 and the second fixing member 60. Hereinafter, a case in which the sensing portion 400 is provided in the first fixing member 20 will be described. The first fixing member 20 may include a first fixing portion 410 and a second fixing portion 420 to be fastened to or separated from each other.

The sensing portion 400 may measure a fastening strength of the first fixing member 20. The sensing portion 400 may include pressure sensors 430 to measure a pressure applied between the first fixing member 20 and the user 1. The pressure sensors 430 may be provided on an inner side surface of the first fixing member 20.

The controller 70 may control the driving source 30 based on information about the pressure measured by the pressure sensors 430. For example, when the measured pressure is greater than or equal to a desired (or, alternatively, a predetermined) reference pressure, the controller 70 may determine that the first fixing member 20 is fixed. Thus, the controller 70 may power on the driving source 30. Conversely, when the measured pressure is less than the reference pressure, the controller 70 may determine that the first fixing member 20 is unfixed. Thus, the controller 70 may power off the driving source 30.

Figure 7:
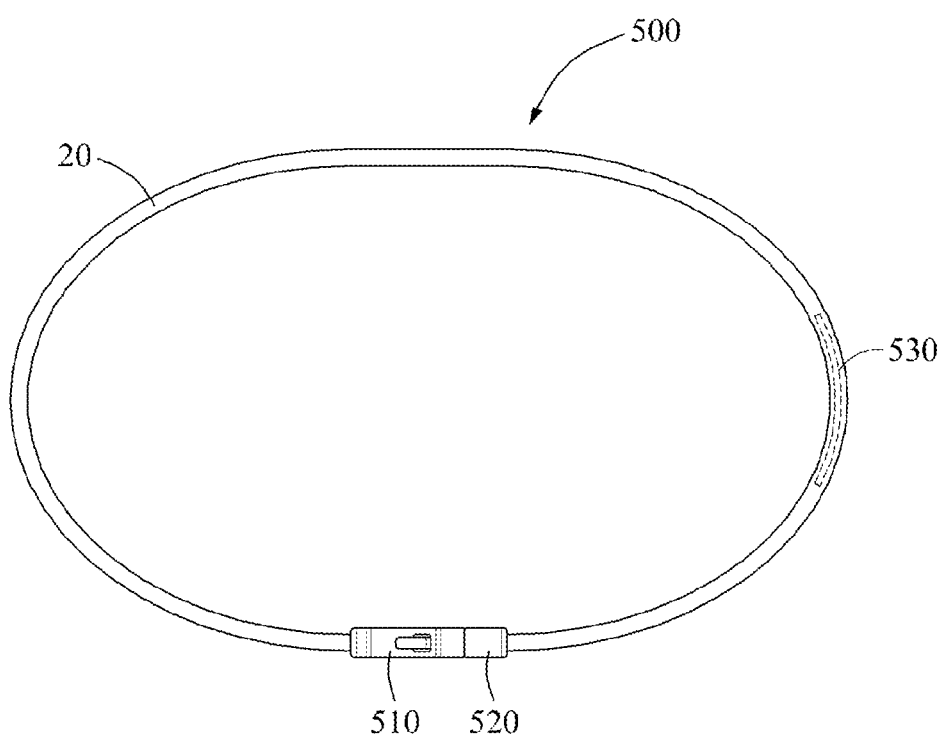
FIG. 7 is a view illustrating a sensing portion according to some example embodiments.

FIG. 7 is a view illustrating a sensing portion 500 according to some example embodiments.

Referring to FIG. 7, the sensing portion 500 may be provided in at least one of the first fixing member 20 and the second fixing member 60. Hereinafter, a case in which the sensing portion 500 is provided in the first fixing member 20 will be described. The first fixing member 20 may include a first fixing portion 510 and a second fixing portion 520 to be fastened to or separated from each other.

The sensing portion 500 may measure a fastening strength of the first fixing member 20. The sensing portion 500 may include a tensile force sensor 530 to measure a tensile force applied to the first fixing member 20. The tensile force sensor 530 may be provided in an internal portion of the first fixing member 20. For example, the tensile force sensor 530 may include a strain gauge. In other example embodiments, the first fixing member 20 may include an air bladder configured to hold an amount of gas therein to supply uniform pressure to the user 1, and the tensile force sensor 530 may be configured to sense a fixing state of the first fixing member 20 by sensing a deformation rate of the first fixing member 20.

The controller 70 may control the driving source 30 based on information about the tensile force measured by the tensile force sensor 530. For example, when the measured tensile force is greater than or equal to a desired (or, alternatively, a predetermined) reference tensile force, the controller 70 may determine that the first fixing member 20 is fixed. Thus, the controller 70 may power on the driving source 30. Conversely, when the measured tensile force is less than the reference tensile force, the controller 70 may determine that the first fixing member 20 is unfixed. Thus, the controller 70 may power off the driving source 30.

Figure 8:
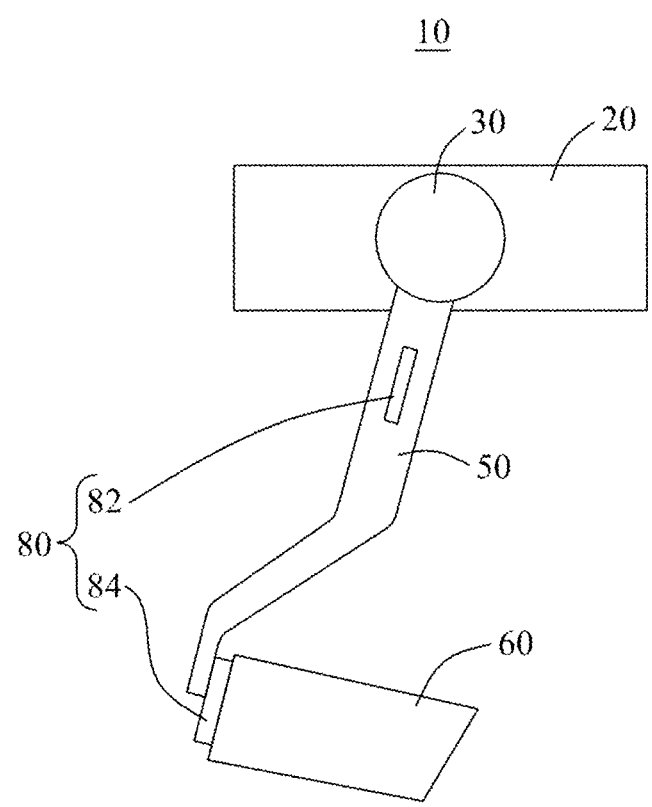
FIG. 8 is a view illustrating a sensing portion according to some example embodiments.

FIG. 8 is a view illustrating a sensing portion 80 according to some example embodiments.

Referring to FIG. 8, the sensing portion 80 may be disposed in the power transmitting member 50. The sensing portion 80 may include a tensile force sensor 82 and/or a pressure sensor 84.

The tensile force sensor 82 may measure a tensile force applied to the power transmitting member 50. The controller 70 may control the driving source 30 based on information on the tensile force measured by the tensile force sensor 82. The tensile force sensor 82 may operate in a similar manner as the tensile force sensor 530, and, therefore, detailed descriptions thereof will be omitted for conciseness.

The pressure sensor 84 may be disposed between the power transmitting member 50 and the second fixing member 60. The pressure sensor 84 may measure a pressure applied between the power transmitting member 50 and the second fixing member 60. The controller 70 may control the driving source 30 based on information about the pressure measured by the pressure sensor 84. The pressure sensor 84 may operate in a similar manner as the pressure sensor 430, and, therefore, detailed descriptions thereof will be omitted for conciseness.

Figure 9:
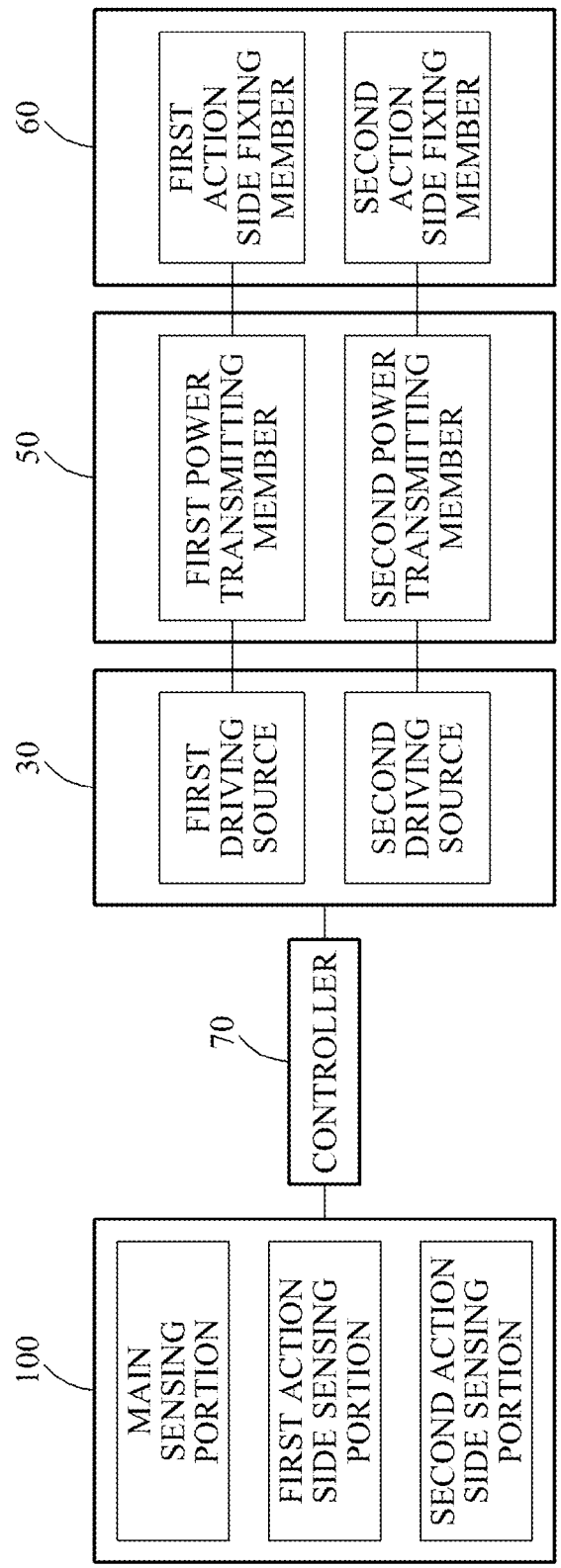
FIG. 9 is a block diagram illustrating a motion assistance apparatus according to some example embodiments.

FIG. 9 is a block diagram illustrating the motion assistance apparatus 10 according to some example embodiments.

Referring to FIG. 9, the motion assistance apparatus 10 may include the main fixing member 20, the driving source 30, the power transmitting unit 50, the action side fixing member 60, the controller 70 and the sensing portion 100.

The action side fixing member 60 may include a first action side fixing member and a second action side fixing member that support different portions of the user 1.

The sensing portion 100 includes a main sensing portion to sense a fixing state of the main fixing member 20, a first action side sensing portion to sense a fixing state of the first action side fixing member, and a second action side sensing portion to sense a fixing state of the second action side fixing member. In some example embodiments, the first and second action side sensing portions may be connected to the first and second active side fixing members, respectively.

The power transmitting member 50 may include a first power transmitting member to transmit power to the first action side fixing member, and a second power transmitting member to transmit power to the second action side fixing member.

The driving source 30 may include a first driving source to drive the first power transmitting member, and a second driving source to drive the second power transmitting member. The first power transmitting member and the second power transmitting member may also be driven by a single driving source.

The controller 70 may control the driving source 30 based on information received from the main sensing portion, the first action side sensing portion, and the second action side sensing portion. The controller 70 will be described in more detail with reference to FIG. 18.

Figure 10:
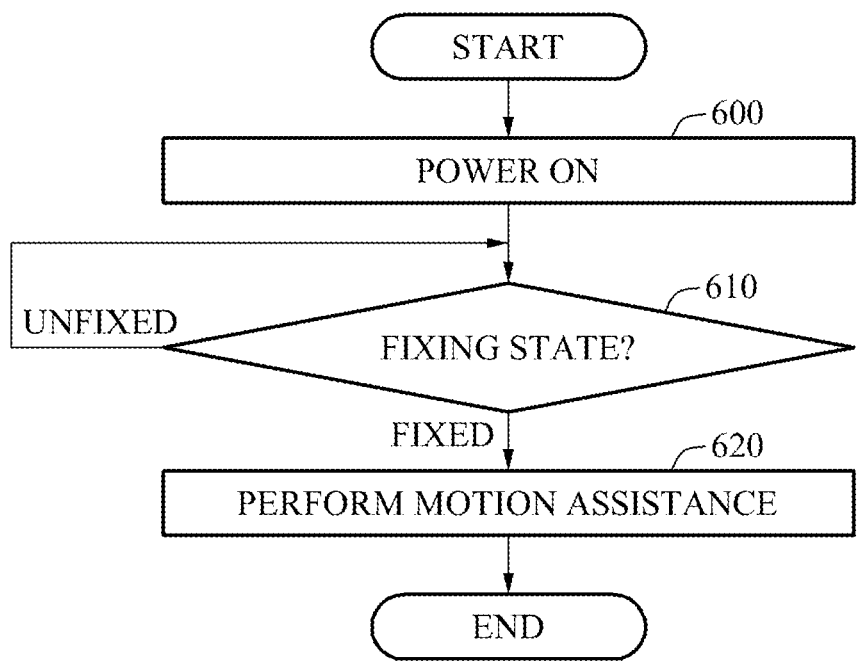
FIG. 10 is a flowchart illustrating a method of controlling a motion assistance apparatus according to some example embodiments.

FIG. 10 is a flowchart illustrating a method of controlling the motion assistance apparatus 10 according to some example embodiments.

Referring to FIG. 10, in operation 600, the controller 70 may power on the motion assistance apparatus 10. In operation 610, the sensing portion 100 may sense a fixing state of the main fixing member 20 or the action side fixing member 60. In operation 620, the controller 70 may perform a motion assistance operation by controlling the driving source 30.

In detail, in operation 600, the controller 70 may power on the motion assistance apparatus 10 in response to a request by a user.

When the motion assistance apparatus 10 is powered on, in operation 610, the sensing portion 100 may sense a fixing state of the main fixing member 20 and/or the action side fixing member 60. When the sensing portion 100 includes a pressure sensor, the sensing portion 100 may measure a pressure applied between a user and the main fixing member 20 and/or the action side fixing member 60, and sense the fixing state of the main fixing member 20 and/or the action side fixing member 60 based on the measured pressure. For example, the sensing portion 100 may include one or more of the sensing portions 100 to 500 described above.

When the sensing portion 100 senses that the main fixing member 20 and/or the action side fixing member 60 is unfixed in operation 610, the controller 70 may instruct the sensing portion 100 to iteratively perform operation 610 to determine when the main fixing member 20 and/or the action side fixing member 60 is fixed. When the main fixing member 20 or the action side fixing member 60 is fixed in operation 610, in operation 610, the controller 70 may control the driving source 30 to perform a motion assistance operation. The motion assistance operation may assist the user 1 in smoothly walking. For example, the motion assistance operation may vary an amount of assistance provided to the user 1 as the user 1 moves through various phases of a walking cycle. For example, the controller 70 may instruct the walking assistance robot to increase the torque if the main fixing member 20 or the action side fixing member 60 is exerting positive work on the leg of the user 1, for example, when the user 1 is increasing a pace of walking on a flat surface, a sloped surface or a stepped surface. Likewise, the controller 70 may instruct the walking assistance robot to increase a damping torque applied to a leg of the user 1, if the main fixing member 20 or the action side fixing member 60 is exerting negative work on the leg of the user 1, for example, when the user 1 is decreasing a pace of walking on the flat surface, the sloped surface or the stepped surface.

In the foregoing control method, the motion assistance apparatus 10 may operate while the main fixing member 20 or the action side fixing member 60 is fixed and thus, a user safety may increase. In addition, without receiving a separate motion assistance instruction, the controller may immediate perform the motion assistance operation when the main fixing member 20 or the action side fixing member 60 is sensed as being fixed while the motion assistance apparatus 10 is powered on and thus, a usability may increase.

Figure 11:
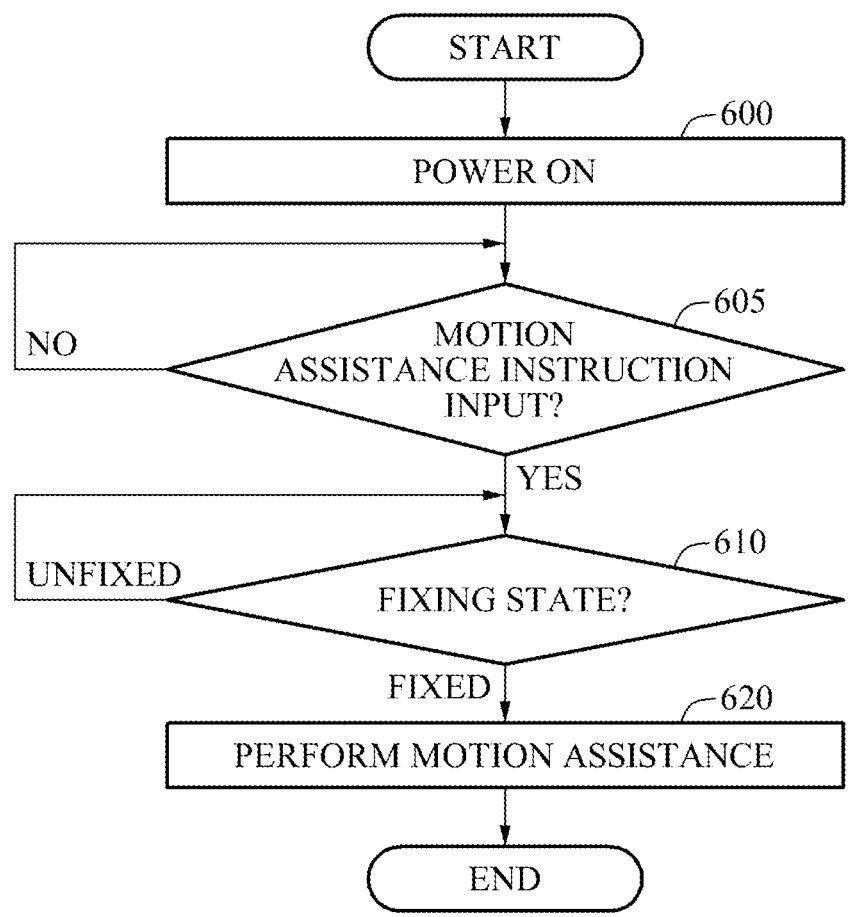
FIG. 11 is a flowchart illustrating a method of controlling a motion assistance apparatus according to some example embodiments.

FIG. 11 is a flowchart illustrating a method of controlling the motion assistance apparatus 10 according to some example embodiments. Duplicated descriptions similar to the descriptions provided with reference to FIG. 10 will be omitted for conciseness.

Referring to FIG. 11, the method of controlling the motion assistance apparatus 10 illustrated in FIG. 11 further includes an operation 605 of receiving a motion assistance instruction, as compared to the method of FIG. 10.

In detail, in operation 600, the controller 70 may power on the motion assistance apparatus 10 in response to an instruction from a user.

When the motion assistance apparatus 10 is powered on, in operation 605, the controller 70 may receive a motion assistance instruction.

The controller 70 may iteratively perform operation 605 until the motion assistance instruction is input into the controller 70. When the motion assistance instruction is input in operation 605, in operation 610, the sensing portion 100 may sense, a fixing state of the main fixing member 20 and/or the action side fixing member 60.

When the main fixing member 20 and/or the action side fixing member 60 is unfixed in operation 610, the controller 70 may instruct the sensing portion 100 to iteratively perform operation 610 to determine when the main fixing member 20 and/or the action side fixing member 60 is fixed. When the main fixing member 20 or the action side fixing member 60 is fixed in operation 610, the controller 70 may control the driving source 30 to perform a motion assistance operation, in operation 620.

In the foregoing controlling method, operation 620 may be performed after two verifications are performed. The motion assistance apparatus 10 may operate in response to an input of a motion assistance instruction and thus, a user manipulability may increase. In addition, when operation 605 is performed prior to operation 610, an unnecessary sensing operation of the sensing portion 100 may be prevented until the motion assistance instruction is input.

While FIG. 11 illustrates that the controller 70 performs operation 605 before operation 610, the controller 70 may perform operation 605 after operation 610 is performed.

Figure 12:
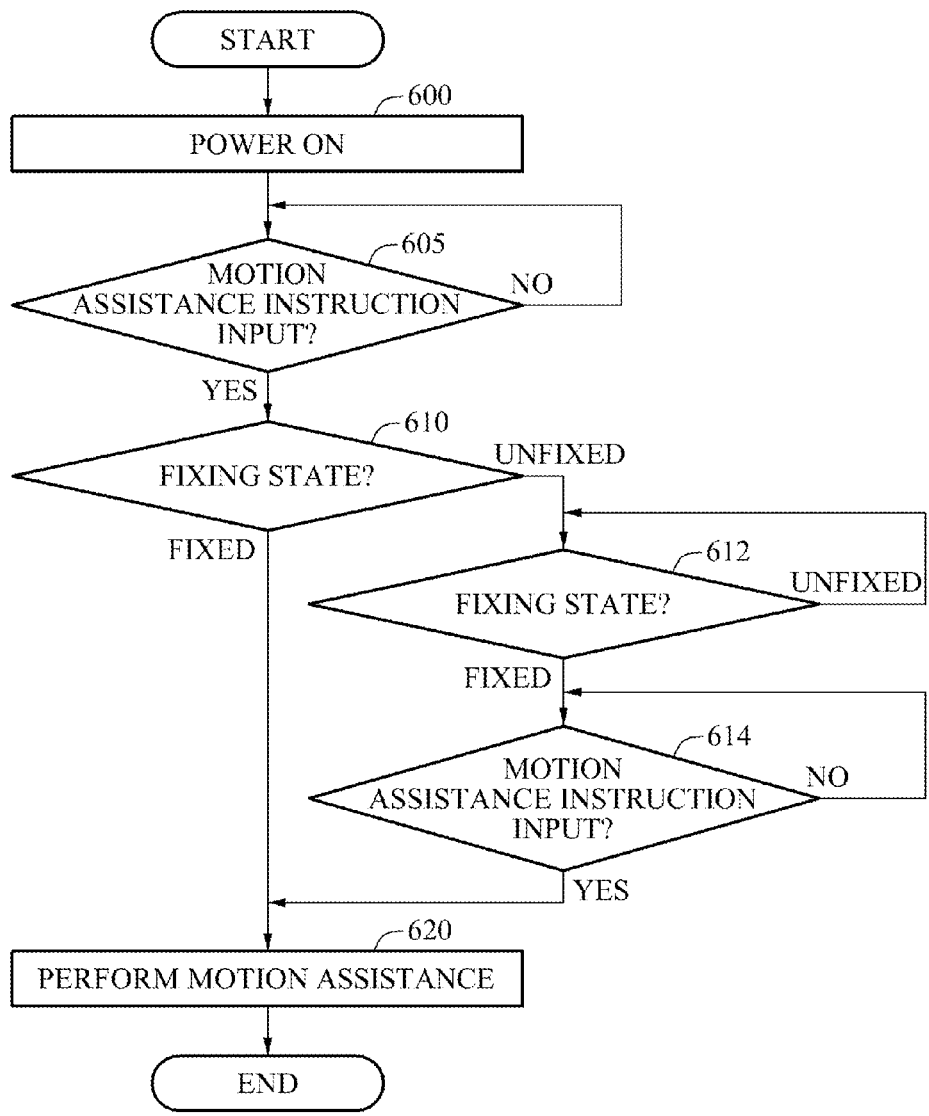
FIG. 12 is a flowchart illustrating a method of controlling a motion assistance apparatus according to some example embodiments.

FIG. 12 is a flowchart illustrating a method of controlling the motion assistance apparatus 10 according to some example embodiments. Duplicated descriptions similar to the descriptions provided with reference to FIGS. 10 and 11 will be omitted for conciseness.

Referring to FIG. 12, the method of controlling the motion assistance apparatus 10 further includes operation 610 of primarily sensing a fixing state of the main fixing member 20 or the action side fixing member 60, operation 612 of secondarily sensing a fixing state of the main fixing member 20 or the action side fixing member 60, and operation 614 of receiving a motion assistance instruction to be performed after operation 612 is performed.

In detail, in operation 610, the sensing portion 100 may primarily sense a fixing state of the main fixing member 20 and/or the action side fixing member 60.

When the main fixing member 20 or the action side fixing member 60 is sensed as being fixed in operation 610, the controller 70 may perform a motion assistance operation in operation 620. In contrast, when the sensing portion 100 senses that the main fixing member 20 or the action side fixing member 60 is unfixed in operation 610, the controller 70 may perform operation 612.

When the main fixing member 20 or the action side fixing member 60 is sensed as still being unfixed in operation 612, operation 612 may be iteratively performed. When the main fixing member 20 or the action side fixing member 60 is sensed as being fixed in operation 612, the controller 70 may perform operation 614.

When the motion assistance instruction is not input in operation 614, the controller 70 may iteratively perform operation 614. When the motion assistance instruction is input in operation 614, the controller 70 may perform a motion assistance operation in operation 620.

Operation 605 of receiving a motion assistance instruction may be performed prior to operation 610. In some example embodiments, operation 605 may be an operation of primarily receiving a motion assistance instruction, and operation 614 may be an operation of secondarily receiving a motion assistance instruction.

In the foregoing control method, the controller 70 may perform a motion assistance operation immediately when the main fixing member 20 or the action side fixing member 60 is sensed as being fixed in operation 610 and thus, usability may increase. In addition, if the controller 70 senses that the main fixing member 20 and/or the action side fixing member 60 is unfixed in operation 610, by preventing an automatic operation of the motion assistance apparatus 10 until a motion assistance instruction is input, the controller 70 may secure a sufficient time to fix the main fixing member 20 or the action side fixing member 60, and, therefore, a user safety may increase.

Figure 13:
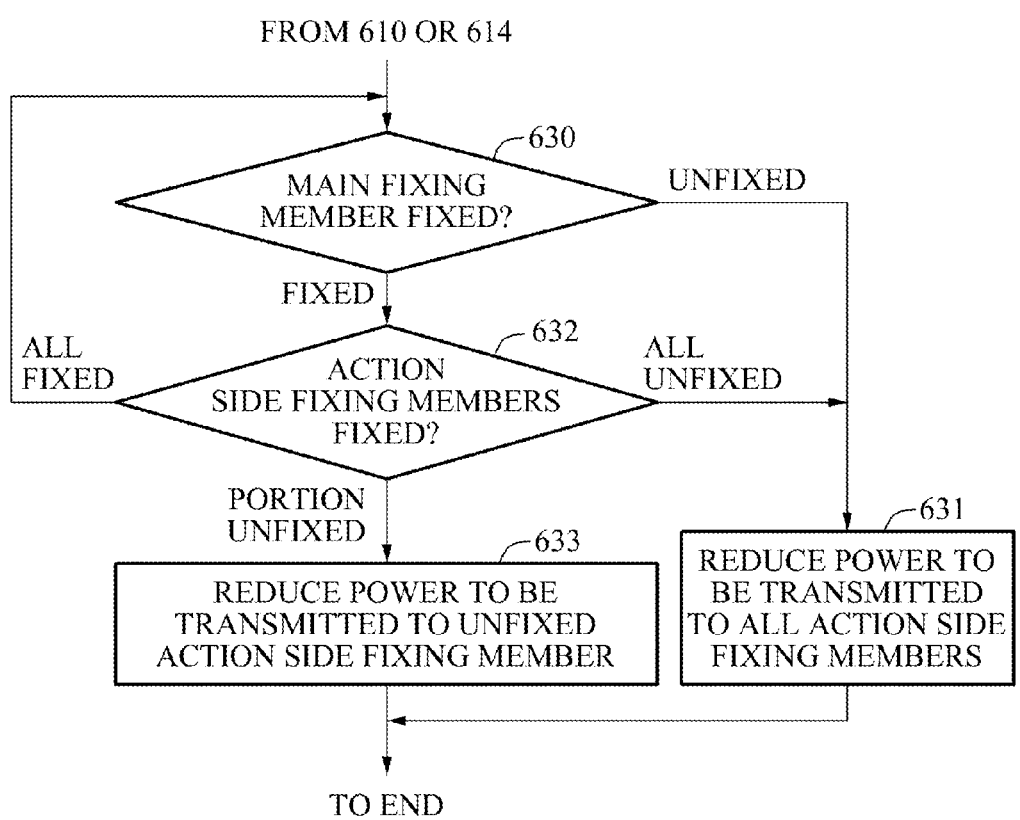
FIG. 13 is a flowchart illustrating a method of controlling a motion assistance apparatus, performed based on a type of an unfixed fixing member, according to some example embodiments.

FIG. 13 is a flowchart illustrating a method of controlling the motion assistance apparatus 10, performed based on a type of an unfixed fixing member, according to some example embodiments.

Referring to FIG. 13, FIG. 13 illustrates performing motion assistance as illustrated in operation 620 of FIGS. 10-12 according to some example embodiments, in which the motion assistance is based on a type of an unfixed fixing member.

The motion assistance of operation 620 may include operation 630 of sensing whether the main fixing member 20 is fixed, operation 632 of sensing whether the action side fixing member 60 is fixed, operation 633 of reducing power to be transmitted to the unfixed action side fixing member 60, and operation 631 of reducing power to be transmitted to all action side fixing members 60.

In detail, in operation 630, the main sensing portion of the sensing portion 100 may sense whether the main fixing member 20 is fixed.

When the main fixing member 20 is sensed as being unfixed in operation 630, the controller 70 may control the driving source 30 to reduce power to be transmitted to all action side fixing members 60, in operation 631. When the main fixing member 20 is sensed as being fixed in operation 630, the action side sensing portion of the sensing portion 100 may sense whether the action side fixing member 60 is fixed, in operation 632.

When all action side fixing members 60 are sensed as being fixed in operation 632, the controller 70 may iteratively instruct the main sensing portion of the sensing portion 100 to iteratively perform operation 630 and monitor whether the main fixing member 20 remains fixed.

When a portion of action side fixing members 60 are sensed as being unfixed in operation 632, the controller 70 may control the driving source 30 to reduce power to be transmitted to the unfixed action side fixing member 60, in operation 633. When all action side fixing members 60 are sensed as being unfixed in operation 632, the controller 70 may control the driving source 30 to reduce power to be transmitted to all the action side fixing members 60, in operation 631.

In the foregoing controlling method, the controller 70 may suspend a motion assistance operation when the main fixing member 20 is unfixed and thus, a user safety may increase. Further, when a portion of the action side fixing members 60 is unfixed while the main fixing member 20 is fixed, by reducing only power to be transmitted to the unfixed action side fixing member 60, a remaining fixed action side fixing member 40 may continuously perform the motion assistance operation. Therefore, even if a part of the motion assistance apparatus 10 malfunctions, the motion assistance apparatus 10 may continuously operate within a safety-secured range. Thus, a usage efficiency of the motion assistance apparatus 10 may increase.

Figure 14:
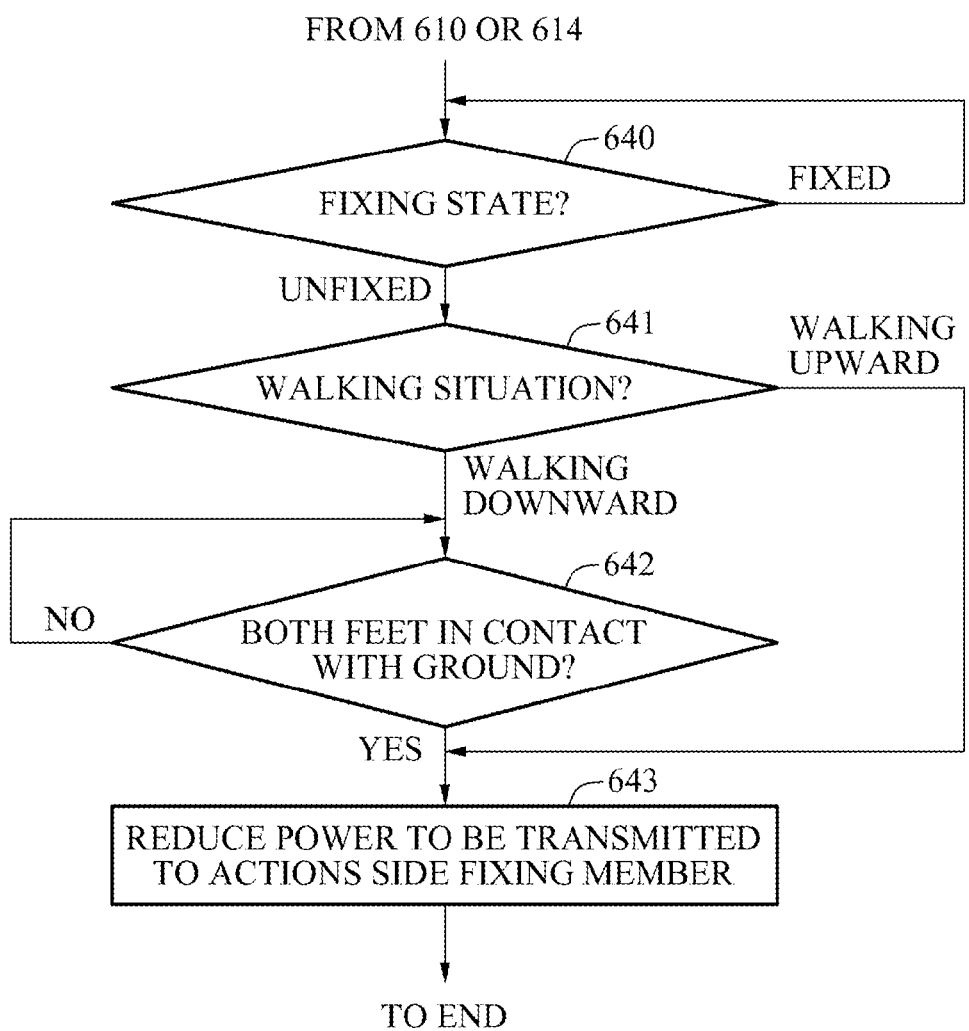
FIG. 14 is a flowchart illustrating a method of controlling a motion assistance apparatus, performed based on a walking situation of a user, according to some example embodiments.

FIG. 14 is a flowchart illustrating a method of controlling the motion assistance apparatus 10, performed based on a walking situation of a user, according to some example embodiments.

Referring to FIG. 14, FIG. 14 illustrates performing motion assistance as illustrated in operation 620 of FIGS. 10-12 according to some example embodiments in which the motion assistance is based on a walking situation of a user.

The motion assistance of operation 620 may include operation 640 of sensing a fixing state of the main fixing member 20 or the action side fixing member 60, operation 641 of sensing a walking situation of a user, operation 642 of sensing whether both feet of the user are in contact with the ground, and operation 643 of reducing power to be transmitted to the action side fixing member 60. For example, in some example embodiments, in an effort to avoid injury to the user 1, even though the fixing member 60 is unfastened, the motion assistance apparatus 10 may continue to perform the aforementioned motion assistance operation when the user 1 is walking downhill and has not stopped and placed both feet on the ground. Therefore, although the fixing member 60 is unfastened while the user is walking downhill, the power transmitting member 50 may prevent a sudden forward jerk of the leg of the user 1.

In detail, in operation 640, the sensing portion 100 may sense whether the main fixing member 20 and/or the action side fixing member is fixed.

When the main fixing member 20 or the action side fixing member is sensed as being unfixed in operation 640, the controller 70 may sense a walking situation of the user, in operation 641.

The walking situation of the user may include a situation in which the user is walking on a slope or stairs in an upward inclined direction, hereinafter referred to as "walking upward", and a situation in which the user is walking on a slop or stairs in a downward inclined direction, hereinafter referred to as a "walking downward". The walking situation may be sensed using an altimeter, an accelerometer, or a motion pattern obtained based on, for example, an angle of rotation of the power transmitting member 50.

When the controller 70 senses that the user is walking upward in operation 641, the controller 70 may reduce the power transmitted to the action side fixing member 60, in operation 643.

When the controller 70 senses that user is walking downward in operation 641, the controller 70 may determine whether both feet of the user are in contact with the ground, in operation 642. Whether a foot of the user is in contact with the ground may be sensed using a pressure sensor, an inertial measurement unit, or an acceleration sensor disposed on the foot of the user. When a pressure measured by the pressure sensor increases beyond a threshold, the controller 70 may sense that the foot of the user is in contact with the ground. In addition, an oscillation occurring when the foot touches the ground may be sensed using an inertial measurement unit or an acceleration sensor.

When both feet of the user are sensed as being not in contact with the ground in operation 642, the controller 70 may iteratively perform operation 642 until both feet of the user contact the ground. When both feet of the user are sensed as being in contact with the ground in operation 642, the controller 70 may reduce the power transmitted to the action side fixing member 60, in operation 643.

While FIG. 14 illustrates operation 642 being performed after operation 641, in some example embodiments, operation 642 may also be performed prior to operation 641 such that, when both feet of the user are in contact with the ground, the controller 70 may reduce the transmitted power in operation 643 immediately without first sensing the walking situation of the user.

In the foregoing control method, in a case of walking downward, which is more dangerous than walking upward, the controller 70 may reduce the assistance power when both feet are in contact with the ground. Thus, an accident happening to the user due to a sudden change in power may be prevented.

Figure 15:
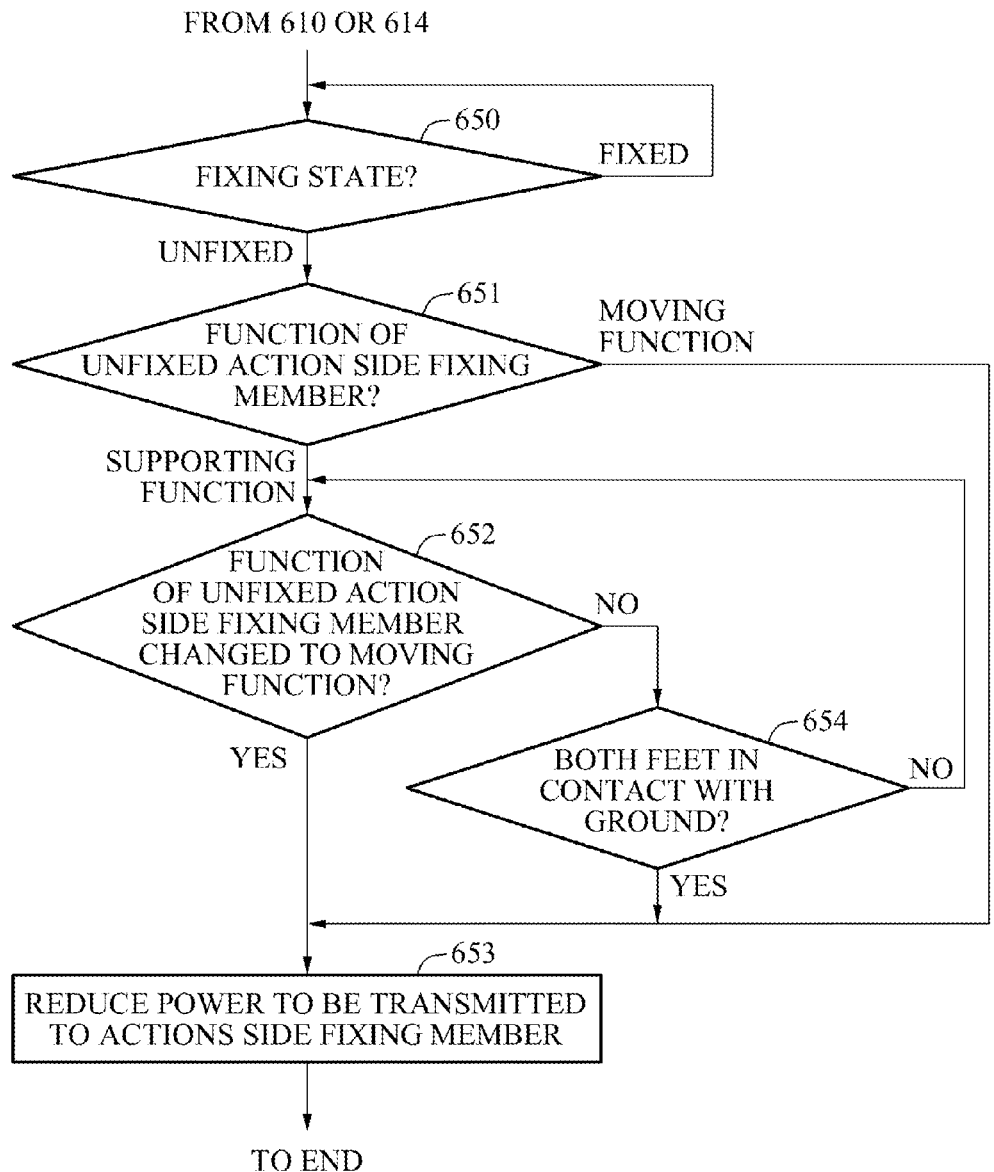
FIG. 15 is a flowchart illustrating a method of controlling a motion assistance apparatus, performed based on a function of an unfixed fixing member, according to some example embodiments.

FIG. 15 is a flowchart illustrating a method of controlling the motion assistance apparatus 10, performed based on a function of an unfixed fixing member, according to some example embodiments.

Referring to FIG. 15, FIG. 15 illustrates performing motion assistance as illustrated in operation 620 of FIGS. 10-12 according to some example embodiments in which the motion assistance is based on a function of an unfixed fixing member.

In some example embodiments, the motion assistance of operation 620 may include operation 650 of sensing a fixing state of the main fixing member 20 or the action side fixing member 60, operation 651 of sensing a function of the unfixed action side fixing member 60, operation 652 of sensing whether the function of the unfixed action side fixing member 60 is changed to a moving function, operation 654 of sensing whether both feet of the user are in contact with the ground, and operation 653 of reducing power to be transmitted to the action side fixing member 60.

In detail, in operation 650, the sensing portion 100 may sense a fixing state of the main fixing member 20 and/or the action side fixing member 60.

The controller 70 may instruct the sensing portion 100 to iteratively perform operation 650 until one or more of the main fixing member 20 and the action side fixing member 60 is sensed as being unfixed.

When the main fixing member 20 or the action side fixing member 60 is sensed as being unfixed in operation 650, the controller 70 may sense a function of the unfixed action side fixing member 60, in operation 651.

The function of the action side fixing member 60 may include a moving function and a supporting function. The moving function may refer to a function of the action side fixing member 60 corresponding to a leg spaced apart from the ground. The supporting function may refer to a function of the action side fixing member 60 corresponding to a leg being in contact with the ground. The function of the action side fixing member 60 may be sensed using a pressure sensor, an inertial measurement unit, or an acceleration sensor disposed on a foot of the user.

When the function of the unfixed action side fixing member 60 corresponds to the moving function in operation 651, the controller 70 may reduce power transmitted to the unfixed action side fixing member 60, in operation 653. When the function of the unfixed action side fixing member 60 corresponds to the supporting function in operation 651, the controller 70 may sense whether the function of the unfixed action side fixing member 60 is changed to the moving function, in operation 652. When the function of the unfixed action side fixing member 60 is changed to the moving function in operation 652, the controller 70 may reduce the power transmitted to the unfixed action side fixing member 60, in operation 653.

When the function of the unfixed action side fixing member 60 is not changed to the moving function in operation 652, the controller 70 may determine whether both feet of the user are in contact with the ground, in operation 654. When both feet of the user are in contact with the ground in operation 654, the controller 70 may reduce the power transmitted to the unfixed action side fixing member 60, in operation 653. When both feet of the user are sensed as being not in contact with the ground in operation 654, operation 652 may be performed.

While FIG. 15 illustrates that operation 654 is performed after operation 651, in some example embodiments, operation 654 may also be performed prior to operation 651 such that, when both feet of the user are in contact with the ground, the controller 70 may reduce the power in operation 653 immediately without sensing the function of the unfixed action side fixing member 60.

Figure 16:
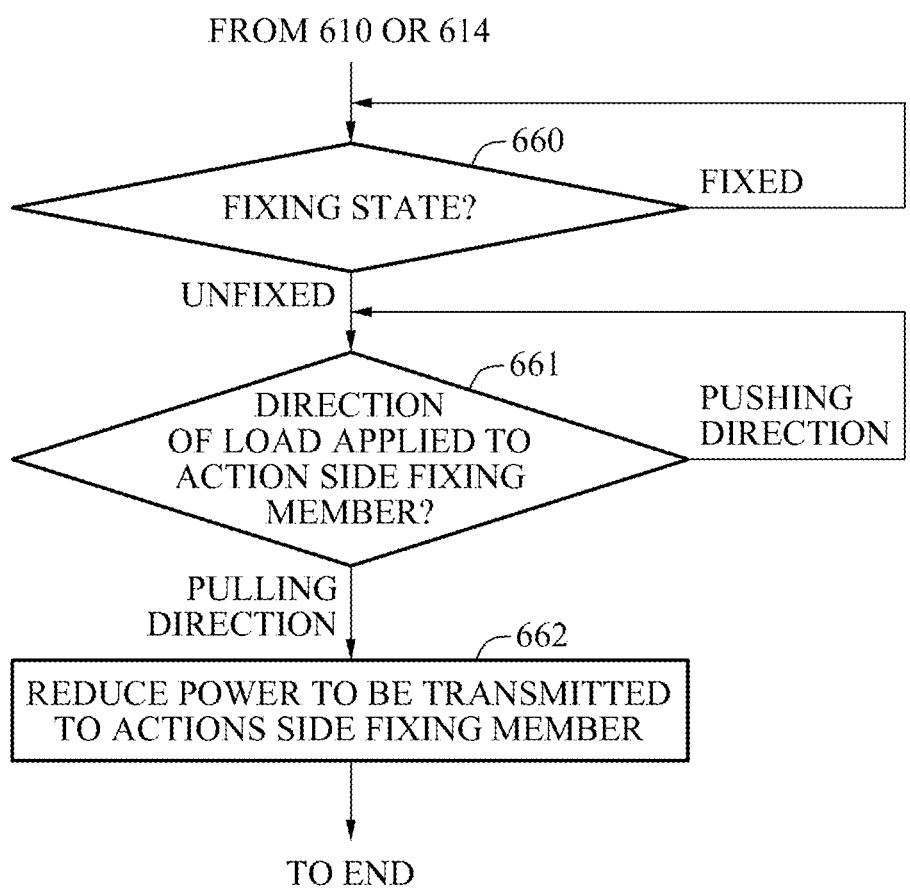
FIG. 16 is a flowchart illustrating a method of controlling a motion assistance apparatus, performed based on a direction of a load applied to an unfixed fixing member, according to some example embodiments.

FIG. 16 is a flowchart illustrating a method of controlling the motion assistance apparatus 10, performed based on a direction of a load applied to an unfixed fixing member, according to some example embodiments.

Referring to FIG. 16, FIG. 16 illustrates performing motion assistance as illustrated in operation 620 of FIGS. 10-12 according to some example embodiments in which the motion assistance is based on a direction of a load applied to an unfixed fixing member.

In some example embodiments, the motion assistance of operation 620 may include operation 660 of sensing a fixing state of the action side fixing member 60, operation 661 of sensing a direction of a load applied to the unfixed action side fixing member 60, and operation 622 of reducing power to be transmitted to the action side fixing member 60.

In detail, in operation 660, the sensing portion 100 may sense a fixing state of the action side fixing member 60.

When the action side fixing member 60 is sensed as being unfixed in operation 660, the controller 70 may detect a direction of a load applied to the unfixed action side fixing member 60, in operation 661. In some example embodiments, the controller 70 may detect that the direction of the load applied by the motion assistance apparatus 10 is a pushing direction, if the fixing member 50 is pushing the user's thighs backward. Likewise, in some example embodiments, the controller 70 may detect that the direction of the load applied by the motion assistance apparatus 10 is in a pulling direction, if the fixing member 50 is pulling the user's thighs forward. As discussed in more detail below, the controller 70 may detect that the direction of the load by detecting if the user's thigh is exerting pressure and/or force against a sensor.

The direction of the load applied to the unfixed action side fixing member 60 may be sensed using a pressure sensor disposed between the power transmitting member 50 and the action side fixing member 60, or a tensile force sensor provided on the power transmitting member 50.

When a value is sensed by the pressure sensor or the tensile force sensor, the controller 70 may verify that the load is applied to the unfixed action side fixing member 60 in a pushing direction. Conversely, when no value is sensed by the pressure sensor or the tensile force sensor, the controller 70 may verify that the load is applied to the unfixed action side fixing member 60 in a pulling direction.

When the direction of the load applied to the unfixed action side fixing member 60 corresponds to the pushing direction in operation 661, the controller 70 may iteratively perform operation 661 until the load is applied in the pulling direction.

When the direction of the load applied to the unfixed action side fixing member 60 corresponds to the pulling direction in operation 661, the controller 70 may reduce the power transmitted to the unfixed action side fixing member 60, in operation 662.

In the foregoing controlling method, by reducing the power transmitted to an action side fixing member 60 substantially incapable of providing a motion assistance force, the controller 70 may reduce the power consumption and increase a user safety. In addition, by continuously transmitting power to an action side fixing member 60 capable of providing a motion assistance force even in an unfixed state, a usage efficiency of the motion assistance apparatus 10 may increase.

Figure 17:
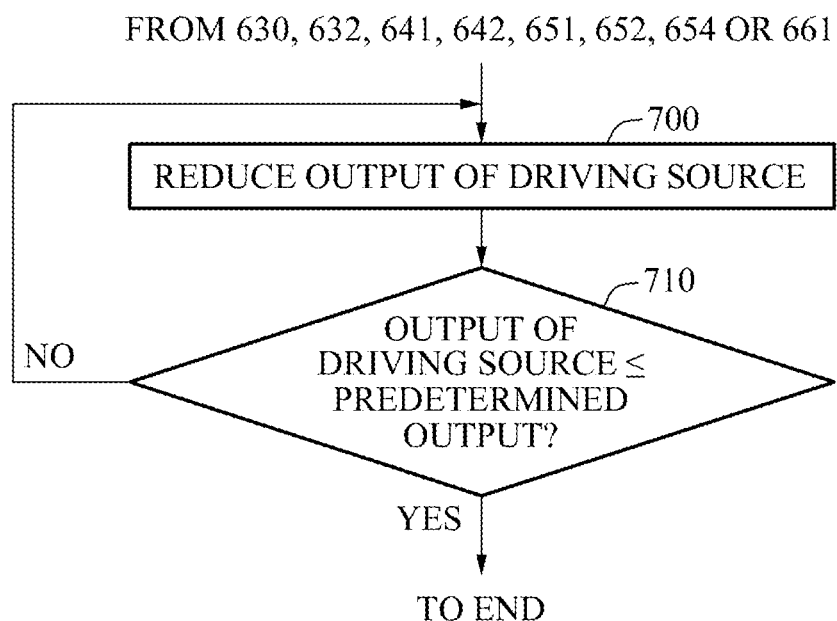
FIG. 17 is a flowchart illustrating an operation of reducing power to be transmitted to an action side fixing member in a method of controlling a motion assistance apparatus according to some example embodiments.

FIG. 17 is a flowchart illustrating an operation of reducing power to be transmitted to the action side fixing member 60 in a method of controlling the motion assistance apparatus 10 according to some example embodiments. Referring to FIG. 17, FIG. 17 illustrates reducing power transmitted to the action side fixing member 60 as illustrated in operations 631, 633, 643, 653, or 662 of FIGS. 13-16 according to some example embodiments. Hereinafter, reducing power as illustrated in operation 631 will be described. However, the following descriptions may also apply to operations 633, 643, 653, or 662.

In some example embodiments, the power reduction of operation 631 may include operation 700 of reducing an output of the driving source 30, and operation 710 of comparing the output of the driving source 30 to a predetermined output.

In detail, in operation 700, the controller 70 may reduce an output of the driving source 30. In operation 710, the controller 70 may determine whether the reduced output of the driving source 30 is less than or equal to the desired (or, alternatively, the predetermined) output.

When the output of the driving source 30 excesses the desired (or, alternatively, the predetermined) output in operation 710, the controller 70 may iteratively perform operation 700 until the output of the driving source 30 is less than or equal to the desired output. When the output of the driving source 30 is less than or equal to the desired (or, alternatively, the predetermined) output in operation 710, the controller 70 may instruct the driving source 30 to continuously transmit power at the corresponding output.

In the foregoing control method, power may be continuously transmitted within a range safe although the main fixing member 20 or the action side fixing member 60 is unfixed. Thus, a usage efficiency of the motion assistance apparatus 10 may increase.

Operations 700 and 710 are provided as only an example of operation 631, 633, 643, 653, or 662. Example embodiments are not limited thereto. In some example embodiments, power to be transmitted to the action side fixing member 60 may be reduced by powering of the motion assistance apparatus 10, by blocking power supplied to the driving source 30, or by holding an operation to maintain a desired (or alternatively, a predetermined) state of the driving source 30.

Figure 18:
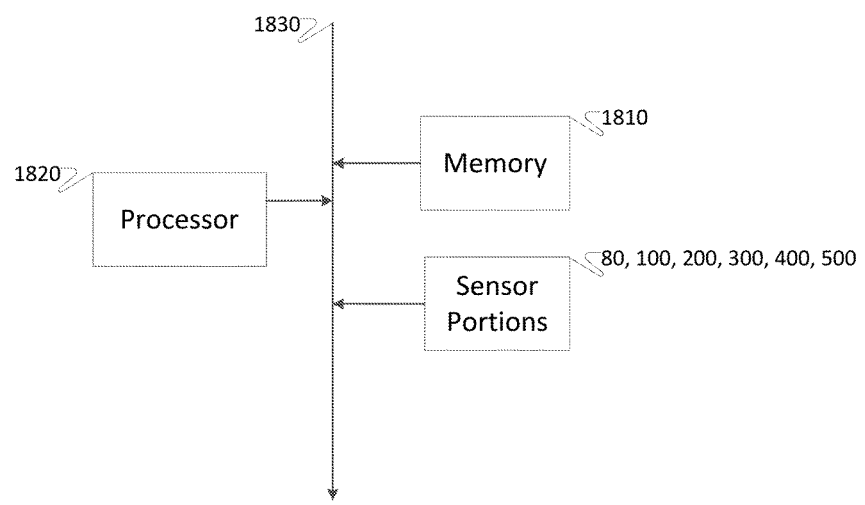
FIG. 18 illustrates a controller according to some example embodiments.

FIG. 18 illustrates a controller according to some example embodiments.

Referring to FIG. 18, the controller 70 may include memory 1810 and a processor 1820 that may send data to and/or receive data from one another using a data bus 1830.

The memory 1810 may be any device capable of storing data. For example, the memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor 1820 may be any device capable of processing data including, for example, a microprocessor configured to carry out specific operations by performing arithmetical, logical, and input/output operations based on input data, or capable of executing instructions included in computer readable code. The processor 1820 may be a logic chip, for example, a central processing unit (CPU), a controller, or an application-specific integrated circuit (ASIC), that when, executing the instructions stored in the memory 1810, configures the processor 1820 as a special purpose machine such that the processor 1820 is configured to determine if one or more of a waist fixing member 20, and leg fixing members 60 are secured to the body of a user 1 using information received from sensor portions 80 and 100 to 500. The processor 1820 may perform motion control 620 when the fixing members 20 and 60 are secured to the body of the user 1 and, thereafter, if one or more of the fixing members 20 and 60 are unfixed, the controller 70 may reduce the power transmitted to the unfixed fixing member 20 and 60 based on various factors.

The processor 1820 may reduce the power transmitted to the unfixed fixing member 20 and 60, for example, when the user 1 is walking on a gradient with both feet on the ground, when the user 1 is one of moving with an unfixed fixing member 20 and 60 and standing still with both feet on the ground, or when a pulling force is applied to the fixing member 60. Therefore, in some example embodiments, the motion assistance apparatus 10 may prevent sudden frontward bounce of the leg of the user 1 by continuing to provide motion assistance to the user while the user is walking downhill and the front of the fixing member 60 is unfixed. Further, in other example embodiments, the motion assistance apparatus 10 may reduce unnecessary power usage by reducing the force applied to the user 1 when the fixing member 60 is unfixed. Further still, in other example embodiments, the motion assistance apparatus 10 may continue to provide motion assistance to the user 1 when the fixing member 60 is unfixed, if the direction of the assistance is a pushing direction so as to extend the amount of time motion assistance is provided to the user.

A number of example embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of controlling a motion assistance apparatus, the motion assistance apparatus including a main fixing member including a first end and a second end, the first end of the main fixing member configured to selectively connect to the second end of the main fixing member to switch the main fixing member from a first unfixed state to a first fixed state in which the main fixing member encircles a first portion of a user, an action side fixing member configured to selectively switch between a second fixed state and a second unfixed state, the second fixed state being a state in which the action side fixing member encircles a limb of the user, a driving source attached to the main fixing member, a power transmitting device configured to transmit power from the driving source to the action side fixing member, and a controller configured to control transmission of the power by the driving source, the method comprising:

sensing, via one or more sensors, whether (i) the main fixing member is set to the first fixed state to encircle the first portion of the user, and/or (ii) the action side fixing member is set to the second fixed state to encircle the limb of the user; and selectively performing, by the controller, a motion assistance operation for the user based on whether data from the one or more sensors indicate that (i) the main fixing member is set to the first fixed state to encircle the first portion of the user, and/or (ii) the action side fixing member is set to the second fixed state to encircle the limb of the user.

2. The method of claim 1, wherein the controller performs the motion assistance operation when the main fixing member is set to the first fixed state and the action side fixing member is set to the second fixed state.

3. The method of claim 2, further comprising:

receiving a motion assistance instruction from the user, wherein the controller performs the motion assistance operation when the motion assistance instruction is received from the user.

4. The method of claim 1, wherein the performing comprises:

reducing the power transmitted to the action side fixing member when the action side fixing member is unfixed such that the power is transmitted from the driving source to the action side fixing member at a reduced level, the reduced level being greater than zero.

5. The method of claim 1, wherein the action side fixing member includes a plurality of action side fixing members, and the performing comprises:

sensing which of the plurality of action side fixing members are in the second unfixed state; and reducing the power transmitted to respective ones the plurality of action side fixing members when the respective ones of the plurality of action side fixing members are in the second unfixed state.

6. The method of claim 1, wherein the performing comprises:

controlling the power transmitted to the action side fixing member based on a direction of a load applied to the action side fixing member, the controlling including, continuously performing the motion assistance operation for the user when the direction of the load is a direction in which the action side fixing member is pushed against the limb of the user by the power irrespective of whether the action side fixing member is in the second fixed state or the second unfixed state;

continuously performing the motion assistance operation for the user when the direction of the load is a direction in which the action side fixing member is pulled away from the limb of the user by the power and the action side fixing member is in the second fixed state; and reducing the power transmitted to the action side fixing member when the direction of the load is the direction in which the action side fixing member is pulled away from the limb of the user by the power and the action side fixing member is in the second unfixed state.

7. The method of claim 1, wherein the performing comprises:

one of stopping the driving source and reducing an output of the driving source to a desired output value.

8. The method of claim 1, wherein the performing comprises:

reducing the power transmitted to the action side fixing member in response to the main fixing member being unfixed.

* * * * *